United States Patent [19]

Sturmer et al.

[11] Patent Number: 4,689,220
[45] Date of Patent: Aug. 25, 1987

[54] IMMUNIZATION BY IMMUNOGENIC IMPLANT

[75] Inventors: Amy M. Sturmer; John L. Sternick, both of Hackensack, N.J.

[73] Assignee: Unigene Laboratories, Inc., Fairfield, N.J.

[21] Appl. No.: 580,856

[22] Filed: Feb. 16, 1984

[51] Int. Cl.[4] .............................................. A61K 39/395
[52] U.S. Cl. ...................................................... 424/85
[58] Field of Search ...................... 424/85, 88, 19, 38; 604/890, 894; 435/172.2

[56] References Cited

U.S. PATENT DOCUMENTS

| 4,391,797 | 7/1983 | Folkman et al. | 424/19 |
| 4,439,199 | 3/1984 | Amkraut et al. | 604/894 |
| 4,455,142 | 6/1984 | Martins et al. | 604/890 |

OTHER PUBLICATIONS

Towbin, H., et al., Proc. Natl. Acad. Sci., vol. 76, pp. 4350–4354, 1979.
Chemical Abstracts, vol. 99, Abstract No. 210861b, 1983.
Styles, T., J. Protozool, vol. 23(2), 1976, 31A.
Chemical Abstracts, vol. 77, Abst. No. 17495c, 1972.
Chemical Abstracts, vol. 94, Abst. No. 90214r, 1981.
Chemical Abstracts, vol. 74, Abst. No. 85682z, 1971.

*Primary Examiner*—Blondel Hazel
*Attorney, Agent, or Firm*—Ostrolenk, Faber, Gerb & Soffen

[57] ABSTRACT

Induction of immune response is achieved by implantation of an antigen-impregnated substrate in the peritoneal cavity of a mammal. Immunogenic implants adapted to be implanted in mammals and the preparation thereof are also disclosed.

3 Claims, No Drawings

IMMUNIZATION BY IMMUNOGENIC IMPLANT

BACKGROUND OF THE INVENTION

This invention relates to an improved method of immunization and, particularly, to an improved method for inducing antibody formation in a host mammal. The invention is also concerned with an immunogenic implant for carrying out the said method. In addition, this invention is concerned with the production of specific immunoglobulins derived therefrom.

It is known that the introduction of antigens by injection into a mammal promotes the formation of antibodies; and this knowledge is the basis of most immunization techniques. The antibodies so produced are proteinaceous substances (immunoglobulins) derived from plasma cell lines and are characterized by classification according to internationally accepted classes for immunoglobulin. Each such class may be further characterized by the antigen against which it is directed.

An antigen broadly may be defined as a substance that can induce an immune response (Alfred Nisonoff, "Introduction to Molecular Immunology," Sinauer Associates Inc., 1982). More strictly, an antigen is a substance containing one or more antigenic determinants, wherein an antigenic determinant is a molecule or portion of a molecule capable of recognizing and binding firmly to the combining site of an antibody. Most naturally-occuring antigens are proteins, although non-proteinaceous material may be antigenic. Also synthetic antigens have been made. A virus particle or a single bacterium normally will contain many different kinds of antigens.

As used herein the term antigen is intended to mean a molecule which will induce a specific immune response, i.e. which will induce the formation of antibodies when introduced into a mammalian host.

Various methods are known in the art for inducing immune response by the injection of antigens.

For example, Stahli et al, Journal of Immunological Methods, Vol. 32 (1980) pages 297–304, dealing with the production of monoclonal antibodies against soluble antigens, describe the maintenance of high concentrations of circulating antigen, for successfully inducing plasma cell formation, by repeated injections.

Nisonoff, "Introduction to Molecular Immunology", 1982, discloses that subcutaneous or intramuscular injection of an emulsion of an antigen and an adjuvant permits prolonged slow release of the antigen and tends to increase the production of antibodies. Suitable adjuvants are alum or complete Freund's adjuvant (a water-in-oil emulsion containing killed mycobacteria and a detergent).

Axen et al, in U. S. Pat. No. Re. 29474, also disclose repeated subcutaneous injections of antigenic protein with complete Freund's adjuvant to produce antibodies in animals.

Wands et al, U. S. Pat. No. 4,271,145, disclose a process for preparing an antibody to a human viral hepatitis antigen which involves an intraperitoneal injection followed by an intravenous injection of the hepatitis antigen. Wands et al also disclose a composition comprising a hybrid continuous cell line for producing an antibody.

East German Patent No. 146,687 to Bundschuh, issued Feb. 25, 1981, discloses the intraperitoneal or intravenous injection of antigen into a host, (i.e. any antibody-producing animal) for the preparation of an antiserum.

Olovnikov et al, Chemical Abstracts, Vol. 64, 1966, Column 16457, disclose protein-cellulose immunosolvents on which protein antigens are chemically bonded to an insoluble carrier. The preparation is subsequently injected into the host and results in prolonged antibody production.

Freund, Annual Review of Microbiology, Vol. 1, 1947, pages 291–308, discloses various adjuvants used in conjunction with antigens to enhance immunization. Administration is by injection.

Gonzalez et al, Compt. Rend. Soc. Biol., Vol. 106, 1931, pages 1006–1008, and Ramon et al, Compt. Rend. Soc. Biol., Vol. 118, 1935, pages 108–111, also disclose the use of adjuvants and show administration only by injection.

Heretofore the procedure recognized for inducing the formation of antibodies was the administration of antigen by injection. Surprisingly, it has now been found that antibodies may be induced in a mammal by the introduction of an implant comprising a predetermined antigen impregnated on a suitable substrate, and that such implantation will promote and facilitate the production of higher titers (greater concentration) of antibodies.

DESCRIPTION OF THE INVENTION

In accordance with the present invention there is provided a new method for the immunization of a mammal to produce a wide variety of antibodies which comprises dissolving a predetermined amount of a soluble antigen in an appropriate solvent, impregnating a porous biologically-compatible substrate with the resulting solution of antigen and implanting the impregnated substrate in the body of the mammal.

The method of the invention is applicable for both high and low molecular weight antigens and results in a much higher concentration of plasma cells producing antigenspecific antibodies.

The substrate impregnated with the antigen may be implanted anywhere within the host but it is preferably implanted into the peritoneal cavity of a mammal.

The invention also provides a method for inducing the formation of antibodies in a mammal which comprises implanting into the peritoneal cavity of the mammal a biologically-compatible substrate, for example, nitrocellulose filter disks, impregnated with a predetermined amount of a soluble antigen. Although nitrocellulose is a preferred substrate, other substrates may be selected, such as glass fiber filters, cotton fibers, nylon mesh filters, as well as other non antigenic inert substances. Indeed, most any conventional non soluble or non-toxic substrate may be employed so long as the antigen remains attached to the substrate. The substrate should also be flexible and not cause undue trauma to the tissues. The dimensions of the substrate are generally not critical and, of course, are dependent both on the particular substrate chosen and the size of the host. For example, when employing nitrocellulose filter paper, a porosity of 0.45 $\mu$m and a diameter of 7 mm would be adequate but these dimensions are merely illustrative of a preferred substrate. The dimensions may be varied considerably depending on the substrate, host cavity dimensions and laboratory conditions and are essentially a matter of empirical determination by conventional means.

The invention further provides an immunogenic implant which comprises a biologically-compatible substrate, for example, nitrocellulose, impregnated with a predetermined amount of a soluble antigen adapted to be implanted in a mammal, preferably into the peritoneal cavity, to induce the formation of antibodies.

The said implant is suitably prepared by dissolving a predetermined amount of a soluble antigen in an appropriate solvent, applying the resulting solution of antigen to a porous, biologically-compatible substrate so that the antigen is absorbed into the substrate and drying the impregnated substrate.

Antigens of various molecular weights may be used, for example, prostaglandin E (330 daltons) and IgM (910,000 daltons). While the invention is applicable to all sizes of antigens, it is particularly advantageous for small antigens (generally those having a molecular weight of less than 10,000 daltons.) Heretofore, these antigens of lower molecular weight had greater difficulty in inducing an immune response.

The concentration of the antigen used for implantation is dependent on its size and antigenicity and usually ranges up to about 15 nanograms, e.g. from 1 nanogram to 15 nanograms. Among the advantages of this implantation method of immunization is the fact that the concentration of antigen may often be reduced from nanograms to picograms, which is several orders of magnitude lower than the concentration used for conventional immunization procedures.

It has been found that the time required for effective immunization using the implantation procedure of the present invention is significantly shorter than that required for standard immunization procedures, for example, injection.

Also the implantation procedure of the present invention results in a lower catabolic rate for antigen decomposition with a corresponding increase in the length of time that the antibody titer is maintained.

The method of the invention further produces a higher number of cells secreting the desired antibody, thereby allowing increased number of positive hybridoma fusions which can be effected in the preparation of monoclonal antibodies and concomitantly increasing the probabilities of the production of antibodies of a specific class.

The immunization method of the invention may be completed in a shorter time than conventional procedures because fewer "boosts" (reintroduction of additional amounts of antigen) are necessary to achieve comparable levels of immunization, i.e. antibody response. Furthermore, the titers (i.e. levels of antibody response) are generally more concentrated than that obtainable by conventional procedures.

The plasma cell lines which result from the introduction of the antigen into the host mammal secrete a variety of antibodies which thereafter may be separated and isolated by conventional procedures as described, for example, in "Monoclonal Antibodies: Hybridomas; A New Dimension In Biological Analysis" edited by R. H. Kennett, et al (Plenum Press, N.Y. 1980).

Antibodies are distinguished by designation according to accepted international classes. Such classification is illustrated in referenced texts including, for example, the Text Book of Immunology by James T. Barrett (3rd Ed., 1978). Such classification recognizes the polypeptide chain structures of an antibody molecule. Such structure comprises two identical light chains and two identical heavy chains. In the intact antibody molecule, the heavy and light chains are bound by disulfide (S-S) bonds. Designations such as IgA, IgM, IgE, IgD and IgG represent specific classes of heavy chains. The designations "λ" (lamda) and "K" (kappa) distinguish the light chains.

The following detailed procedure illustrates the manner in which the invention may be performed using human calcitonin as the antigen, although variations thereof may be readily apparent to those of ordinary skill in the art.

The antigen which is to be used is solubilized in an appropriate buffer solution at a known concentration, and a predetermined amount is deposited on the substrate, in accordance with the following example:

EXAMPLE I

Antigen Preparation and Implantation

1. The antigen employed was lyophilized synthetic human calcitonin (molecular weight=3400 daltons). It was reconstituted at a concentration of 1 mg/ml in phosphate buffered saline without $Ca++$ and $Mg++$. Other non-denaturing solvents can be used as long as the solvent itself is not antigenic or toxic. Examples are alcohol, ether, weak acids and bases.

2. 15 $\mu$l (15 ng) of the solubilized antigen was adsorbed onto nitrocellulose filter disks of 0.45 $\mu$m porosity and 7 mm diameter. The nitrocellulose disks were cut from a large sheet of nitrocellulose filter paper with a hole puncher. The nitrocellulose was carefully handled with forceps and did not come into contact with organic materials, in order to prevent contamination.

3. The antigen-coated disks were dried either overnight at room temperature or in an oven at 50° C. for one hour.

4. 10 Balb/$_{cj}$ mice, 6–8 weeks old, were prepared for surgery. They were anesthetized with ether and their abdomens disinfected with 70% alcohol.

5. A small incision was made through the abdominal wall with sterile instruments.

6. The antigen-coated nitrocellulose disks were inserted through the incision into the abdomen with forceps.

7. The incision was surgically closed with autoclips and the mice were allowed to recuperate.

8. First, second and third boosts were given with antigen-coated nitrocellulose implants at one week intervals post initial immunization. The concentration of the antigen on the boost filters is the same as that used for the immunization.

9. The first hybridization was performed with 5 immunized spleens three days after the second boost while a second hybridization was performed with the remaining immunized spleens three days following the third boost.

EXAMPLE II

Determination of Antibodies and Efficiency of Procedure

To determine the production of monoclonal antibodies to human calcitonin, hybridomas were screened for antibody production using an 125I radioimmunoassay procedure. (Radioimmunofiltration assay by V & P Scientific, Inc., San Diego, Ca. 92122). In the first hybridization, 37% of the wells were positive for hybridomas of which 26.4% produced antibodies. Of this 26.4%, 61.9% were specifically producing antibodies to human calcitonin. In the second hybridization, 62.5% of the wells were positive for hybridomas of which 33.5% produced antibodies. Of these antibody producing hybrids, 70.8% specifically produced antibodies to human calcitonin.

EXAMPLE III

Production of Immunoglobulin (Antibodies)

Antigen used for Immunization

Human form synthetic calcitonin from Sigma Chemical Co.

Method of Immunization

BALB/$c_j$ mice received an immunization of 7.5 μg human calcitonin implanted intraperitoneally (I.P.), on nitrocellulose discs. Two weeks later the mice were boosted I.P. with the same amount and one week past the initial boost a second identical boost was given. After 3 days, the splenocytes were collected for fusion.

Parental cell line (Myeloma) used for fusion

NSI cells were fused to splenocytes with 40% polyethylene glycol 1000.

Selection and cloning procedure

Fused cells were plated in 24 well plates in the presence of a feeder layer (splenocytes and thymocytes) in HAT medium containing 20% heat inactivated fetal calf serum and Garamycin. Cells were cloned by limiting dilution and 1:1 (cell:well) dilution in 96 well plates. Screening was performed with a solid phase radioimmunoassay system using the V & P disposable microfold system with 125I protein A, 125I goat anti-mouse Ig's and 125I rabbit antimouse IgG.

EXAMPLE IV

Identification of immunoglobulins Produced by Example III

The immunoglobulin produced by Example III was separated and isolated as follows:

Using a limiting dilution procedure, cells are cloned at decreasing concentrations per well (starting with a high concentration of 100 cells per well down to a theoretical concentration of 0.75 cells per well.) Next, a 1:1 dilution is performed, whereby cells are distributed in a microtiter plate at a one cell per well ratio. This procedure is repeated three times. Finally bulk culture of the cloned hybrids is carried out in order to mass produce the hybrid cells derived from each clone. The foregoing separation resulted in the isolation of the following immunoglobulins (antibodies):

1. IgM
2. IgM, K
3. IgG 2a, K
4. IgG 2b, K

Antibodies identified above as 1 and 2 may have the same subclass designation but differ according to epitope specificity (each binds to a different portion of the calcitonin molecule). Each antibody so produced may be further identified as specific to synthetic human calcitonin.

I claim:

1. A method for inducing the formation of antigen specific antibodies in a mammal which comprises the steps of implanting in the mammal a biologically-compatible nitrocellulose substrate having an antigen adsorbed thereon.

2. A method according to claim 1 wherein said nitrocellulose is implanted into the peritoneal cavity of the mammal.

3. A method according to claim 1, in which the antigen is human calcitonin.

* * * * *